United States Patent
Kietzmann et al.

(10) Patent No.: US 10,215,786 B2
(45) Date of Patent: Feb. 26, 2019

(54) SENSOR ARRANGEMENT FOR A PACKAGING OF A MEDICAMENT

(71) Applicant: SANOFI-AVENTIS DEUTSCHLAND GMBH, Frankfurt (DE)

(72) Inventors: Hardy Kietzmann, Frankfurt am Main (DE); Jasmin Groeschke, Frankfurt am Main (DE); Hanno Juhnke, Frankfurt am Main (DE); Jan-Peter Spengler, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 635 days.

(21) Appl. No.: 14/367,828

(22) PCT Filed: Dec. 20, 2012

(86) PCT No.: PCT/EP2012/076318
§ 371 (c)(1),
(2) Date: Jun. 20, 2014

(87) PCT Pub. No.: WO2013/092823
PCT Pub. Date: Jun. 27, 2013

(65) Prior Publication Data
US 2015/0108964 A1    Apr. 23, 2015

(30) Foreign Application Priority Data
Dec. 23, 2011 (EP) .................................. 11195529

(51) Int. Cl.
*G01R 27/02* (2006.01)
*H01L 51/00* (2006.01)
(Continued)

(52) U.S. Cl.
CPC .............. *G01R 27/02* (2013.01); *G01J 1/02* (2013.01); *G01K 3/04* (2013.01); *G01K 7/01* (2013.01);
(Continued)

(58) Field of Classification Search
CPC ........... G01R 27/02; G01J 1/02; G01K 13/00; G01K 3/04; G01K 7/00; G01K 7/01;
(Continued)

(56) References Cited

U.S. PATENT DOCUMENTS

| 4,198,851 A | 4/1980 | Janata |
| 4,892,834 A * | 1/1990 | Rauh .................... G01N 27/227 |
| | | 324/71.6 |

(Continued)

FOREIGN PATENT DOCUMENTS

| CN | 2158578 Y | 3/1994 |
| CN | 101212947 | 7/2008 |

(Continued)

OTHER PUBLICATIONS

English Translation of Abstract of Chinese Patent Application No. CN 2158478 dated Oct. 19, 2015.
(Continued)

*Primary Examiner* — Lee Rodak
(74) *Attorney, Agent, or Firm* — McCarter & English, LLP

(57) ABSTRACT

The present invention relates to a sensor arrangement to monitor at least one ambient parameter, the sensor arrangement comprising: a first layer exhibiting a first electrical conductivity, and at least a second layer exhibiting a second electrical conductivity different than the first electrical conductivity and being at least partially in direct contact with the first layer, wherein the first and the second layer in an initial configuration comprise different concentrations of a (Continued)

diffusible component, having an impact on the conductivity of the first and/or the second layer.

18 Claims, 4 Drawing Sheets

(51) Int. Cl.
*G01N 25/56* (2006.01)
*G01N 33/15* (2006.01)
*G01K 13/00* (2006.01)
*G01K 3/04* (2006.01)
*G01J 1/02* (2006.01)
*G01K 7/01* (2006.01)
*G01N 33/00* (2006.01)

(52) U.S. Cl.
CPC .............. *G01K 13/00* (2013.01); *G01N 25/56* (2013.01); *G01N 33/0027* (2013.01); *G01N 33/15* (2013.01); *H01L 51/00* (2013.01)

(58) Field of Classification Search
CPC   G01K 7/015; G01K 7/16; G01K 7/18; G01N 25/56; G01N 33/0027; G01N 33/15; H01L 51/00
USPC .................................................. 324/71.1–71.6
See application file for complete search history.

(56) References Cited

U.S. PATENT DOCUMENTS

| | | |
|---|---|---|
| 5,501,744 A | 3/1996 | Albright et al. |
| 5,975,758 A * | 11/1999 | Yokota .................... G01K 7/183 338/25 |
| 6,065,869 A * | 5/2000 | Lin .......................... G01K 7/16 219/390 |
| 6,077,712 A | 6/2000 | Livingston |
| 7,534,034 B2 | 5/2009 | Clemens et al. |
| 7,551,058 B1 | 6/2009 | Johnson et al. |
| 8,052,932 B2 | 11/2011 | Han et al. |
| 9,027,387 B2 | 5/2015 | Blackburn et al. |
| 2003/0034870 A1 | 2/2003 | Becka et al. |
| 2004/0196050 A1 | 10/2004 | Lurtz |
| 2006/0203882 A1 * | 9/2006 | Makela .................... G01K 3/04 374/161 |
| 2008/0063027 A1 | 3/2008 | Galli |
| 2008/0138926 A1 | 6/2008 | Lavine et al. |
| 2008/0187021 A1 * | 8/2008 | Haarer .................... G01K 3/04 374/102 |
| 2009/0028213 A1 * | 1/2009 | Kund .................... G01K 3/005 374/178 |
| 2009/0093785 A1 | 4/2009 | Brown et al. |
| 2011/0057791 A1 * | 3/2011 | Durgin .................... G01K 3/04 340/539.27 |
| 2012/0175604 A1 | 7/2012 | Hanna et al. |

FOREIGN PATENT DOCUMENTS

| | | |
|---|---|---|
| CN | 1870174 A | 11/2009 |
| EP | 0780672 A1 | 6/1997 |
| EP | 2505978 A1 | 10/2012 |
| JP | S58-152042 A | 9/1983 |
| JP | S62-212560 A | 9/1987 |
| JP | S63-238546 A | 10/1988 |
| JP | H11-237357 A | 8/1999 |
| JP | 2001-074690 A | 3/2001 |
| JP | 2004-503271 A | 2/2004 |
| JP | 2004514919 A | 5/2004 |
| JP | 2004219080 A | 8/2004 |
| JP | 2006-304533 A | 11/2006 |
| JP | 2009-150713 A | 7/2009 |
| JP | 2010513934 A | 4/2010 |
| JP | 2011501127 A | 1/2011 |
| SU | 1762210 A1 | 9/1992 |
| TW | 200834898 | 8/2008 |
| WO | 0075649 A1 | 12/2000 |
| WO | 02/05039 A1 | 1/2002 |
| WO | 2011034206 A1 | 3/2011 |

OTHER PUBLICATIONS

Danzhi Li, The Semiconductor Transformation of Perovskite Ceramics and the Humidity Sensing Mechanism Thereof, Electronic Components and Materials Apr. 1998, vol. 7 No. 2, p. 29-34, dated Apr. 30, 1988.

Semi-conductive Photoelectric Conductor, Baidy Library, dated May 10, 2010.

English Translation of the Abstract of Chinese Patent Application No. 1870174 dated Feb. 13, 2017.

* cited by examiner

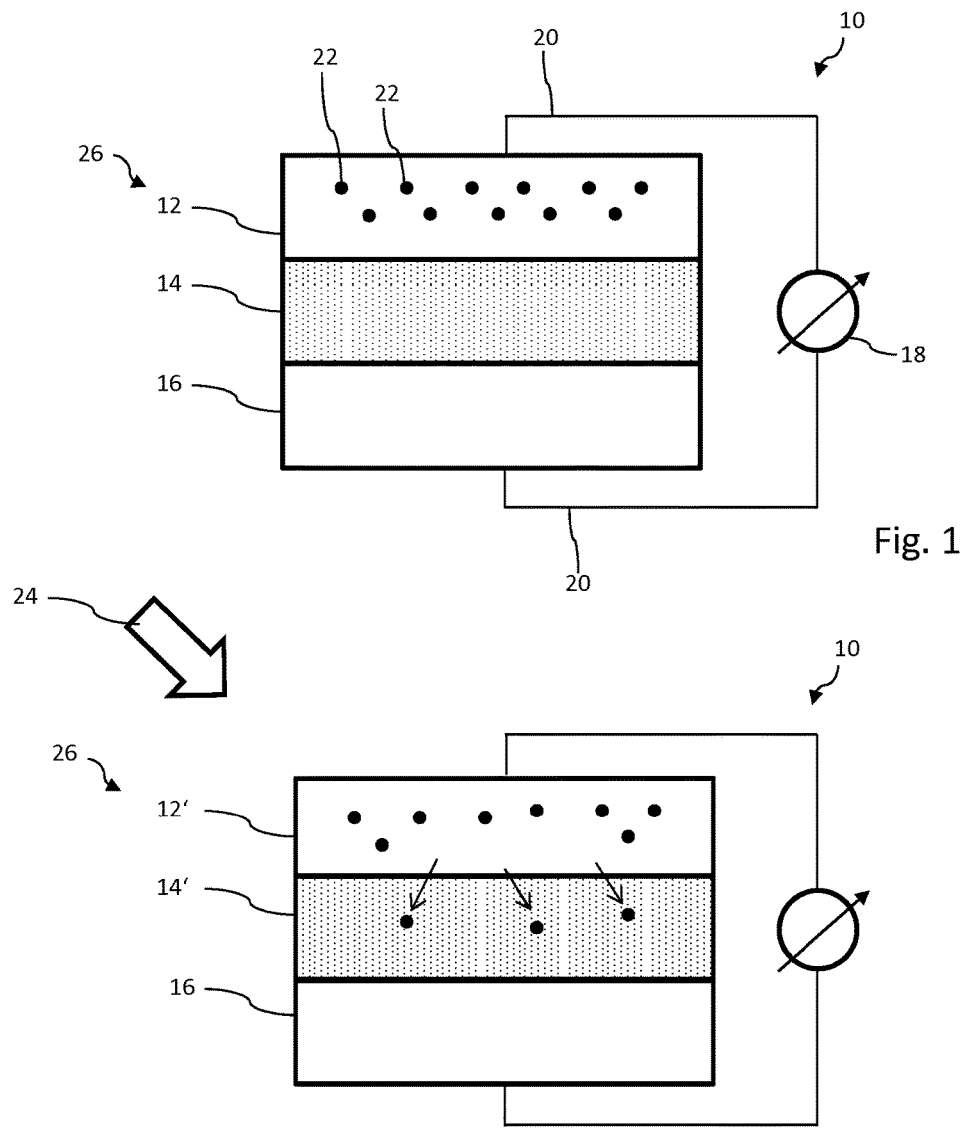

SENSOR ARRANGEMENT FOR A PACKAGING OF A MEDICAMENT

CROSS REFERENCE TO RELATED APPLICATIONS

The present application is a U.S. National Phase application pursuant to 35 U.S.C. § 371 of International Application No. PCT/EP2012/076318 filed Dec. 20, 2012, which claims priority to European Patent Application No. 11195529.0 filed Dec. 23, 2011. The entire disclosure contents of these applications are herewith incorporated by reference into the present application.

FIELD OF INVENTION

The present invention relates to the field of sensors and sensor arrangements to detect and to monitor at least one ambient parameter or ambient condition to which a medicament or a packaging of a medicament is exposed. In particular, the present invention relates to sensor arrangements to be integrated into a primary or secondary packaging of a medicament to monitor ambient parameters, such like temperature, exposure to light, humidity, or presence of particular substances, preferably gaseous substances, over a comparatively long time interval.

BACKGROUND

Medicaments, such as pharmaceutical products have to be kept and stored in a predefined way. Many medicaments require for instance constant refrigeration and must not be kept or stored above a predefined maximum temperature. Moreover, some medicaments are rather sensitive to bright illumination and should therefore be kept in a rather dark or dimmed environment. Other medicaments are rather sensitive to humidity and should be therefore not exposed to humidity.

Depending on their exposure to ambient parameters, such like temperature, illumination and humidity, particular medicaments may become subject to an irreversible degradation process. It is therefore of importance to label such medicaments with a best before date, after which the medicament should no longer be used and applied. The best before date is typically provided on a secondary or primary packaging of the medicament. The best before date has to be determined in such a way, that the medicament can still be used at the given date given that it has been transported and stored appropriately. The best before date, prior to which the medicament should be used is calculated and determined on the basis of the general degradation properties of said medicament and its time of production.

However, if a medicament which is sensitive to heat and illumination is always kept in a dimmed and/or refrigerated environment, the medicament may be of further use even after passing of the best before date. However, since it is generally not possible or impractical to non-destructively test the medicament, respective amounts of medicaments will be discarded after a lapse of their best before date, simply as a precaution and irrespective of the actual constitution of the medicament.

In another scenario, the medicament might be temporarily exposed to inadmissible ambient parameters and may therefore exhibit premature degradation even prior to its best before date. Since such degradation of a medicament may not be discernible by medical staff or end users, there exists a certain danger or hazard, that a prematurely degraded medicament is administered to a patient. Such administering may constitute a hazard to the health of the patient.

In the rare event, a particular medicament turns out to constitute a health risk, as a precaution, those medicaments that where produced in the same batch have to be traced and have to be discarded for safety reasons. Hence, up to now there exists no sufficient and reliable monitoring system to determine the actual state and usability of individual medicaments in a non-destructive way.

It is therefore an object of the present invention to provide a simple and cost-efficient sensor arrangement allowing to monitor ambient parameters to which a medicament and/or its first or secondary packaging has been exposed to. The sensor arrangement should be able to provide qualitative and quantitative information about the actual status and constitution of the medicament. Moreover, the sensor arrangement should be adapted to monitor physical and analytical parameters on the basis of negligible power consumption or even without power consumption.

SUMMARY

The present invention provides a sensor arrangement to monitor at least one ambient parameter to which the sensor arrangement is exposed to. The sensor arrangement comprises a first layer exhibiting a first electrical conductivity and further comprises at least a second layer exhibiting a second electrical conductivity. First and second electrical conductivities are different in magnitude and the first and second layers are at least partially in direct mechanical contact with each other. Preferably, first and second layers comprise an even and flat shaped geometry and are arranged in a mutual contact configuration, in which upper and/or lower planar surfaces of first and second layers at least partially mutually abut.

Additionally, the first and the second layer, at least in an initial configuration, comprise different concentrations of a diffusible component. The diffusible component, i.e. its concentration in the first and/or in the second layer has a measurable impact on the conductivity of first and/or second layers. Additionally, the diffusible component is sensitive to the at least one ambient parameter to be monitored with the present sensor arrangement. In other words, the diffusion process of the diffusible component is governed or at least influenced by the ambient parameter the sensor arrangement is exposed to.

Regarding the diffusible component, the sensor arrangement features a concentration gradient across the interface of first and second layers, which, depending on the magnitude, intensity and/or duration the sensor arrangement is exposed to the ambient parameter, levels out or mutually adjusts. In effect, the concentration of the diffusible component is subject to modification due to detrimental ambient conditions. A modification of the concentration of the diffusible component in the first and/or in the second layer leads to a measurable modification of the electrical conductivity of respective layers, which can be readily measured and detected by means of a suitable measurement device.

The diffusion process taking place between first and second layers itself does not require supply of electrical or mechanical energy. Hence, the sensor arrangement becomes subject to a measurable diffusion process even without energy consumption. Only determination of a resulting change of electrical conductivity of first and/or second layers may require application of respective electrical signals. Generally, the diffusion process to take place between first and second layers may be monitored during the entire life cycle of the medicament. Depending on the type of ambient parameter to be monitored with the sensor arrangement, the diffusion process may even be suitable to integrate the ambient parameter over time, thereby allowing to determine e.g. the total amount of thermal energy to which the sensor arrangement has been exposed to for a predefined time interval.

In a preferred embodiment, the diffusion behaviour, in particular the velocity of the diffusible component is affectable and/or controllable by the magnitude and/or intensity of the ambient parameter. Moreover, the diffusion behaviour and the progress of diffusion depends on the duration, the sensor arrangement is exposed to the respective ambient parameter.

This way, the sensor arrangement is generally adapted to provide qualitative and quantitative information about the progress of the diffusion process, which is an indicator on the magnitude, intensity and duration of exposure to the respective ambient condition.

According to another preferred embodiment, the diffusible component is either embedded in or is arranged at the first layer. The diffusible component initially present in or on the first layer is furthermore adapted to diffuse towards or to diffuse even into the second layer. First and second layers as well as the diffusible component are particularly designed with respect to each other to provide a well-defined and reproducible diffusion process at given ambient parameters. Preferably, first and second layers comprise a crystalline structure, in which the diffusible component is embedded as impurity or defect. Hence, the diffusion process may exhibit an interstitial or substitutional mechanism, generally referred to as lattice diffusion.

According to another preferred embodiment the sensor arrangement further comprises a third layer being at least partially in direct contact with a surface of the second layer that faces away from the first layer. Preferably, the second layer is sandwiched between first and third layers, wherein the layers are arranged on top of each other and are further arranged in a parallel way. Preferably, first, second and third layers form a stack of layers, wherein the various single layers comprise substantially identically-shaped contact surfaces. The third layer may comprise a similar or identical material compared to the first layer. Moreover, compared to the first layer, also the third layer may exhibit a similar or identical concentration of a diffusible component. It is also conceivable, that only the first layer comprises the diffusible component and that the third layer comprises a similar or identical but substantially undoped material.

In still another preferred embodiment, the first layer and the third layer are electrically connectible to a measurement device in order to determine the conductivity of the second layer which is sandwiched therebetween. In such a configuration, first and third layers may comprise or provide electrical contacts, preferably at a side facing away from the second layer. By means of these contacts, a conductivity of the second layer sandwiched between first and third layers can be conveniently measured with an appropriate measurement device, which is for instance adapted to determine the electrical conductivity or resistivity of the second layer.

In still another aspect, the ambient parameter to be monitored by the sensor arrangement is either the ambient temperature, an ambient illumination or radiation and/or ambient humidity. In case the sensor arrangement is adapted to measure temperature and/or illumination, the diffusion processes dependence on thermal- or radiation energy which is deposited to the first, to the second and/or to the third layer is effectively exploited. Depending on the choice of materials for the first, second and/or third layers and/or depending on the choice of the diffusible component, the diffusion process may also be directly or indirectly governed by ambient humidity, which may be monitored accordingly. Accordingly, the sensor arrangement may be also applicable to measure presence and/or concentration of particular gaseous substances that are present in the vicinity of the sensor arrangement.

The sensor arrangement may exhibit a particular sensitivity regarding selected spectral ranges of the electromagnetic spectrum. Typically, the sensor arrangement is able to detect electromagnetic radiation in the UV spectral range, in the visible as well as in the infrared spectral ranges. Moreover, the diffusion process may be designed to become particularly sensitive to selected spectral ranges in particular to the visible and UV spectral range. This way, exposure to UV or visible light can be monitored.

In a further preferred aspect, the first and/or the third layer comprise a conducting or semiconducting material provided with a diffusible dopant substance. Preferably, first and/or third layers are made of a semiconducting material in form of crystalline solids or in form of amorphous or liquid semiconductors. Suitable semiconductor materials are for instance crystalline silicon but also hydrogenated amorphous silicon as well as mixtures of arsenic, selenium and tellurium in a variety of proportions. Other available and generally suitable semiconductor materials may comprise a combination of chemical elements of the third and fifth main group, such like GaP, GaAs, InP, InSb, InAs, GaSb, GaN, AlN, InN, $Al_xGa_{1-x}As$, $In_xGa_{1-x}N$ and/or of the second and sixth main group, such like ZnO, TnS, ZnSe, ZnTe, CdS, CdSe, CdTe, $Hg_{(1-x)}Cd_{(x)}Te$, BeSe, BeTe, HgS. Moreover, the first and/or the third layer may also comprise a III-VI semiconductors, such like GaS, GaSe, GaTe, InS, InSe, InTe, I-III-VI semiconductors, such like $CuInSe_2$, $CuInGsSe_2$, $CuInS_2$, $CuInGaS_2$ and/or IV-IV semiconducting materials, such like SiC or SiGe.

Additionally or alternatively, the first and/or the third layer may also comprise organic semiconducting materials, such like Tetracen, Pentacen, Phthalocyanine, Polythiophene, PTCDA, MePTCDI, Chinacridon, Acridon, Indanthron, Flavanthron, Perinon, Alq3, Polyvinylcarbazol or TCNQ.

Dending on the semiconducting material selected for the first and/or for the third layer, the choice of a diffusible dopant substance may vary. For instance, with silicon or germanium, elements of the third main group, such like boron, indium, aluminum or gallium may provide a p-doped semiconducting layer. Alternatively, first and/or third layers can also be n-doped by embedding phosphor, arsenic or antimony into the semiconducting material.

With organic semiconducting materials, selective carbon atoms in a chain structure of respective polymers could be substituted to provide intermediate energy levels in a respective energy band of such molecules. In particular, electrically conductive polymers, such like Polyaniline (PANI) may form a basis to provide a humidity sensing arrangement, since such organic semiconducting materials typically exhibit a degradation when exposed to water and/or oxygen.

In a further preferred embodiment, the second layer typically sandwiched between the first and the third layer is substantially non-conductive in an initial configuration. The second layer features an increased conductivity when absorbing or receiving diffusible components from the first and/or from the third layer.

Additionally, it is of particular benefit, when the diffusible component or the dopant substance is initially embedded or provided in or at the first and/or in or at the third layer. This way, a concentration gradient between the first and the second layer and/or between the third and the second layer can be established which induces a respective diffusion process once the ambient parameter of relevance triggers or accelerates the diffusion process.

In a further preferred embodiment, the dopant substance comprises a molecular component exhibiting a chemical reaction when exposed to $H_2O$. This way, an effective humidity sensing configuration can be provided, wherein the dopant substance is adapted to chemically react with $H_2O$ and wherein at least one residual component of the dopant substance, e.g. molecular oxygen may exhibit a diffusion process with regard to the first, second and/or third layer, which leads to a measurable modification of the electrical conductivity of the second layer.

In a further preferred embodiment, the second layer comprises at least two opposite or opposing surface segments comprise contact surfaces of different sizes with the adjacently arranged first and third layers. It has turned out, that the diffusion process can be manipulated and even controlled by the size of the contact surface between first and second layer or between third and second layer, respectively. Generally, the magnitude of the measurable diffusion enlarges with an increasing contact surface. By way of suitable modifications of mutually abutting contact surfaces of respective layers, the general diffusion behaviour of the diffusible component can be modified and controlled, e.g. in order to shift the sensitivity of the sensor arrangement towards lower or larger values or ranges of the measurable ambient parameter.

It is of further benefit, when according to another embodiment the first and/or the third layer comprise at least two geometrical mutually non-overlapping structures lying in the plane of a respective layer and being separated by a filling material or by a void space. It is of particular benefit, when the first and/or the third layer comprise one or several, for instance triangular or rectangular shaped geometrical structures in order to provide particular surface segments of a respective layer featuring differently sized contact surface segments, each of which exhibiting a different sensitivity of diffusion regarding the respective ambient parameter.

It is further of advantage when the conductivity of the second layer disposed between electrically insulated first and third layers is measured on the basis said surface segments. For determining the electrical conductivity of the second layer, the various contact surface segments of the first and/or of the third layer are preferably separately coupled with a measurement device in order to the determine their electrical conductivity and the degree of diffusion individually.

The surface segment of first and/or third layers may be arranged in a two-dimensional grid, which may be of regular or irregular type.

Here, it is further of advantage, when at least one geometrical structure of the first layer traverses at least one geometrical structure of the third layer in a projection parallel to a surface normal of the first and/or of the third layer. The geometrical structures as well as the layers in which these structures are embedded in are not in direct contact with each other but are separated by the initially insulating second layer.

However, since the geometrical structures of first and third layer at least partially overlap, numerous overlapping regions of different size can be provided, each of which exhibiting a different degree of sensitivity regarding the ambient parameter to be monitored. In this way, the measurable range of the ambient parameter as well as the time interval, the sensor arrangement can be used to continuously monitor said ambient parameter can be extended.

Moreover, it is also conceivable, that different geometrical structures of the first layer or of the third layer exhibit a different concentration of a diffusible component. Moreover, it is conceivable, that various geometrical structures of a common layer comprise different semiconducting materials doped with different diffusible dopants. Also in this way, the measurable range of the sensor arrangement may be extended.

In a further preferred embodiment, the first layer and the third layer of the sensor arrangement comprise a substantially identical geometric shape. Moreover, the first layer is rotated by a predefined angle with respect to the third layer with respect to a rotation axis extending substantially parallel to the surface normal (z) of first and/or third layer. The angle of rotation of first and third layer may be governed by the specific geometric shape of the geometric structure of respective layers. In case the layers comprise several parallel oriented triangular-shaped geometric structures, the layers may for instance be rotated by about 90 degree.

Typically, the rotation axis may be located in the centre of the surface of first and/or third layer, such that the lateral extension of layers and/or the stack of layers remains substantially unaffected by said mutual rotation. In this context it may be of particular benefit, when the layers are of substantially quadratic shape.

According to another embodiment, it may be of further advantage when the geometrical structures of the first layer and the third layer form a pattern comprising at least two surface segments of different size. Moreover, especially in a rotated configuration, e.g. a 90° rotated constellation, the pattern may comprise a particular symmetry featuring at least two surface segments of equal size. This way, a certain redundancy can be provided. Also, the measurable conductivity of the second layer in regions of overlapping surface segments of substantially equal size can be generally used to determine an average value, thereby allowing to increase the precision and reliability of the sensor arrangement.

In still another preferred embodiment, the sensor arrangement further comprises an electric antenna circuit and/or a processing unit. The antenna circuit, the processing unit and the stack of layers may be integrated into a single chip, which itself may be integrated into or attached to a primary or secondary packaging of a medicament. For instance, the antenna and/or the processing unit may be designed as components to wirelessly communicate with further analysis devices, such like RFID readers or the like.

Moreover, if the antenna circuit is for instance designed to receive and/or to transmit RF signals, the entire sensor arrangement may be integrated into an RFID chip assembly, which may extract required electrical energy for the determination of the electrical conductivity of the second layer from an externally applied RF field.

Additionally, the invention reflects in a packaging to accommodate or to receive and/or to store at least one item therein and further comprises at least one sensor arrangement as described above. The packaging may be designed for storage of food or beverages as well as for medicaments. In general, the packaging is designed to keep and/or to store items and substances that can become subject to degeneration or deterioration. In particular, the packaging comprises a secondary or primary packaging for a medicament. For instance, the primary packaging may comprise a vitreous body being at least partially filled with a liquid medicament. For instance, the primary packaging may comprise a bottle, an ampoule, a carpule, a cartridge or a syringe. Additionally, the secondary packaging may comprise an injection device being equipped with the primary packaging, e.g. in form of a cartridge filled with the medicament. Alternatively or additionally, the secondary packaging may also comprise a casing to receive a plurality of medicaments or respective medical devices.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39); or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, -continued H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 ]Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in greater detail by making reference to the drawings, in which:

FIG. 1 schematically illustrates a cross section of the sensor arrangement in an initial configuration, FIG. 2 is indicative of the sensor arrangement after or during exposure to ambient conditions.

DETAILED DESCRIPTION

Figure 3:
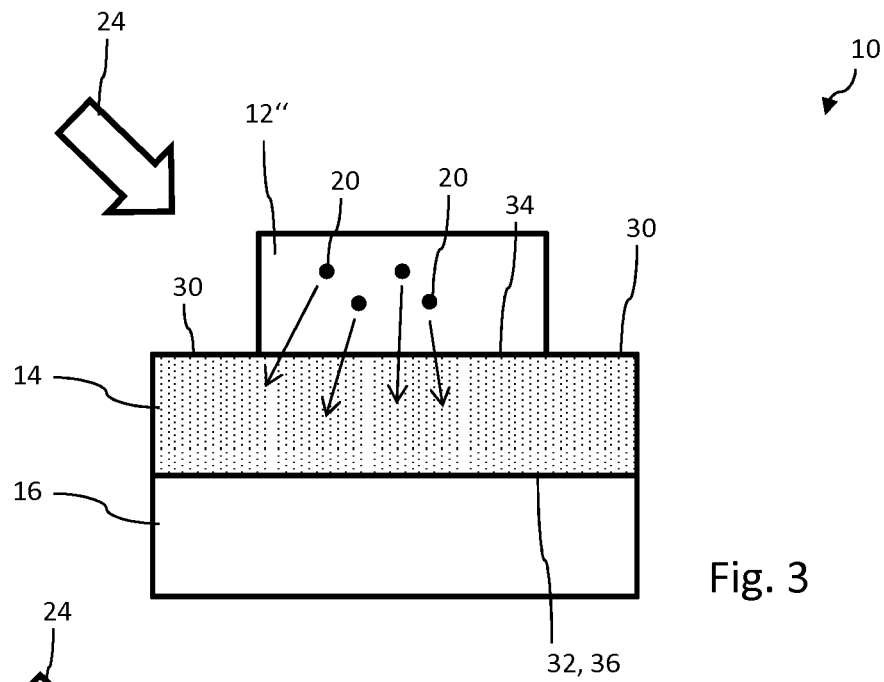
FIG. 3 shows another sensor arrangement with a first layer having a reduced contact surface and FIG. 4 shows a sensor arrangement with an increased first layer.

The sensor arrangement as schematically shown in cross section in FIGS. 1 to 4 comprises a stack 26 of three substantially overlapping layers 12, 14, 16. Here, a first layer 12 comprises numerous diffusible components 22 embedded therein, which under exposure to a particular ambient parameter 24 start to diffuse into the adjacent second layer 14', as indicated in FIG. 2. As a consequence of this diffusion process, the second layer 14' may exhibit a modified electrical inductivity compared to the second layer 14 as shown in FIG. 1 in its initial configuration. This modification in conductivity is generally measurable by a respective measurement device 18 being in electrical contact with the first layer 12 and with the third layer 16 via contacts 20.

The outer layers, hence first layer 12 and third layer 16, may comprise a semiconducting material and may be n- or p-doped by the diffusible dopant substance 22. The diffusion process, which may be influenced by temperature, by intensity of radiation illumination or by humidity 24 may stop or at least slow down when an equilibrium of the concentration of the diffusible component 22 establishes in the first layer 12' and in the second layer 14'.

In order to monitor and to measure the magnitude and duration of the ambient parameter 24, the concentration of the diffusible component 22 as well as the semiconducting materials of first and third layers 12, 16 have to be chosen appropriately. Depending on the type of medicament to which the present sensor arrangement 10 is to be attached to, the material and diffusible component may be chosen and arranged in such a way, that the diffusion process starts or accelerates when a threshold of a respective ambient parameter 24 is traversed, for instance, when the ambient temperature rises above or drops below a predetermined temperature 24.

As long as the sensor arrangement is kept and stored below or above a predefined temperature, hence, within a predefined temperature range, the diffusion process will not be measurable, even after a comparatively long period of time. But as soon as the ambient temperature 24 traverses the predefined threshold, the diffusion process will at least slowly start. As the temperature 24 further rises, e.g. above a second predefined temperature, the diffusion process may accelerate accordingly until an equilibrium configuration is reached. Depending on the degree of diffusion, the conductivity of the second layer to be measured with the measurement device 18 may become subject to respective measureable changes. Since the general diffusion behaviour of the diffusible component is known and/or scaled, the measureable degree of diffusion can give sufficient information about the time and/or the intensity the sensor arrangement 10 has been exposed to the ambient parameter.

In case that the second layer 14 comprises a substantially non-conductive material, its conductivity may rise and its electrical resistivity may decrease the more diffusible particles 22 penetrate the interface between first layer 12 and second layer 14. The diffusion behaviour may be particularly designed and adapted to the chemical or physical degradation properties of the respective medicament. Hence, the actual and inevitable degradation process of the medicament may be mapped and imaged by the sensor arrangement.

Figure 4:
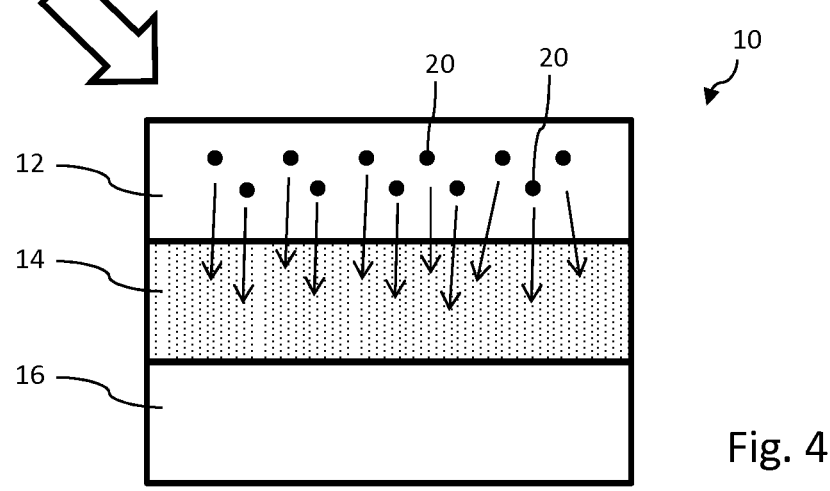

The illustrations of FIGS. 3 and 4 demonstrate the influence of the size of adjacent layers 12", 14 on the magnitude of the diffusion process. Here, the second layer 14 comprises surface 30 being substantially identical in size to the layer's lower surface or lower surface 32. However, only a surface segment 34 of the upper surface 30 is in direct contact with the first layer 12". Therefore, the degree and magnitude of the diffusion process as well as the total number of diffusible particles 22 diffusing towards and into the second layer 14 from the size-reduced first layer 12" is reduced compared to the embodiment as illustrated in FIG. 4, where respective contact surfaces of the first layer 12 and the second layer 14 are substantially identical.

Even though not particularly illustrated it is also conceivable, that not only the first layer 12 but also the third layer 16 can be initially provided with the same or with another diffusible component 22 which is adapted to diffuse towards the second layer 14. In the sketch of FIG. 3, the lower contact surface 36 of the second layer 14 is almost identical to and completely overlaps with a corresponding upper contact surface of the third layer 16.

Figure 5:
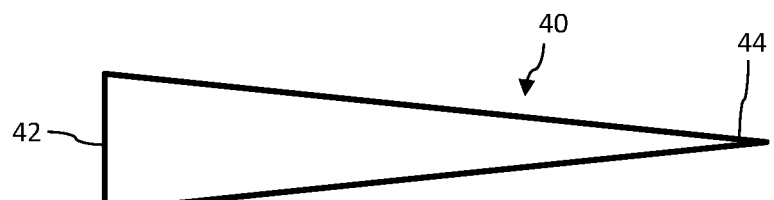
FIG. 5 shows a triangular-shaped geometrical structure of the first and/or the third layer and FIG. 6 schematically illustrates a crossed configuration of first and third layers, each of which having a several triangular-shaped geometric structures, and FIG. 7 schematically illustrates the sensor arrangement equipped with an antenna and a processing unit.
Figure 6:
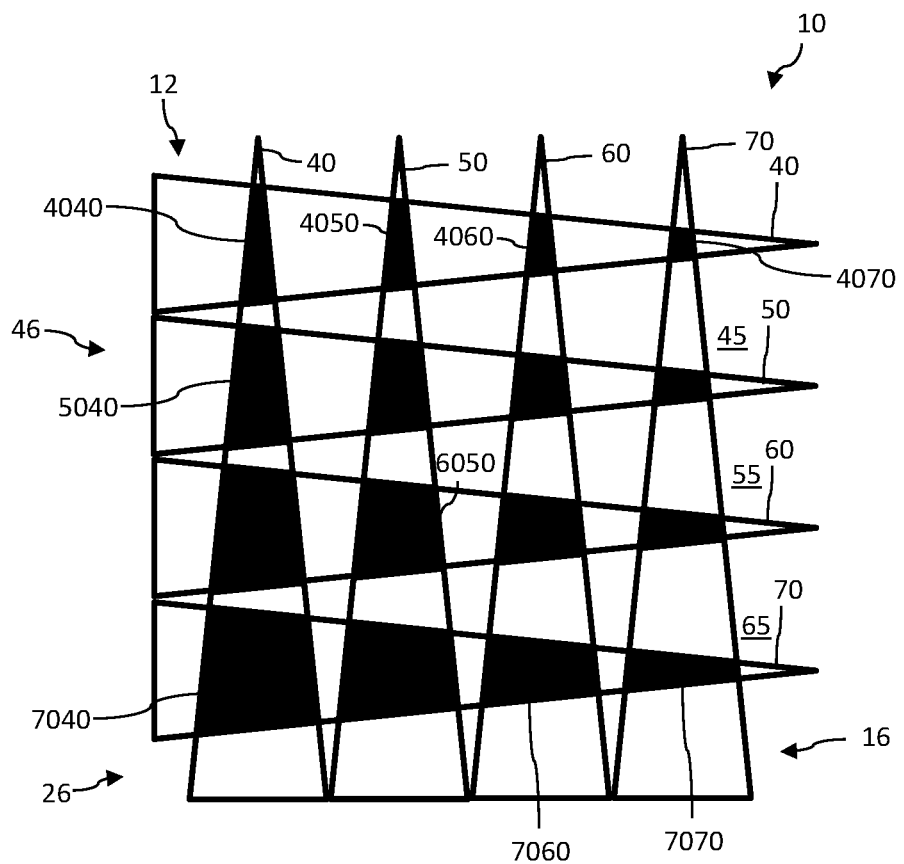

Another way of spatially modifying the degree of diffusion across the interfaces between adjacently disposed layers 12, 14, 16 is indicated in FIGS. 5 and 6. FIG. 5 is illustrative of a particular geometrical structure 40 having a triangular shape and featuring a rather wide end section 42 to the left and a rather small and tipped end section 44 at its opposite end illustrated to the right in FIG. 5. As further shown in FIG. 6, the first layer 12 may comprise four adjacently disposed and identically shaped geometrical structures 40, 50, 60, 70 having a respective void space 45, 55, 65 therebetween. Instead of a void space it is also conceivable to fill the planar gap between adjacently arranged geometrical structures 40, 50, 60, 70 with a different, substantially inert material. As further shown in FIG. 6, the third layer 16 comprises a comparable or substantially identical geometrical structure. Hence, also the third layer 16 comprises four geometrical structures 40, 50, 60, 70, each of which featuring a triangular shape and being adjacently arranged in the plane of the layer.

As further shown in FIG. 6, the two layers 12, 16 of substantially identical shape are mutually rotated by about 90° in order to generate a pattern 46 of surface segments, of which a few segments 4040, 4050, 4060, 4070, 5040, 6050, 7040, 7060 are exemplary indicated in the FIG. 6. Here, the geometrical structures 40, 50, 60, 70 of first and third layers 12, 16 substantially overlap in a projection along a surface normal (z) of first and/or third layer 12, 16. The pattern 46 as shown in FIG. 6, in which substantially overlapping surface segments 40, 50, 60, 70 of first and third layers 12, 16 mutually overlap are indicated as black areas.

Due to the triangular geometrical structures 40, 50, 60, 70 the sizes of these surface segments 4040, 4050, 4060, 4070, ... mutually vary. In effect, and due to their different size, the surface segments 4070 and 7040 for instance exhibit a different general diffusion behaviour, which leads to different local modifications of the electrical conductivity of the second layer 14 disposed therebetween. It may be of further benefit here, when also the second layer 14 comprises a patterned structure that generally corresponds to the pattern of overlapping surface segments 4040, 4050, 4060, 4070, 5040, 6050, 7040, 7060, ... as shown in FIG. 6. In this way, the measurable range of the sensor arrangement as well as the time period, the sensor is capable to monitor a diffusion process can be extended.

When the sensor arrangement 10 as shown in FIG. 6 is designed as a temperature monitoring arrangement, the surface segment 4070 may exhibit a larger diffusion susceptibility compared to a rather small surface segment 7040. As a consequence and as a non-limiting example, the surface segment 7040 may reach an equilibrium configuration and hence a maximum conductivity when exposed to about 30° C. for more than 24 hours. In comparison to that, the surface segment 4070 may exhibit a comparable conductivity only after an exposure to at least 36° C. for more than 7 days.

The residual surface segments may each provide a sensitivity between these two extreme samples. In effect, the sensor arrangement 10 featuring a multiplicity of surface segments of different size may cover a rather large temperature range and a rather large time interval including several months or even years. It is of particular benefit, that some diffusion processes are rather inactive below a predefined threshold temperature but may increase in an exponential way as soon as the temperature rises above such a threshold.

In this context it is to be noted that a comparable diffusion behaviour may be also observed when exposing the sensor arrangement in a brightly illuminated or in a rather humid environment, or when exposing the sensor arrangement in the vicinity of particular gaseous substances, which are themselves adapted to penetrate and to diffuse into the any one of the layers 12, 14, 16.

Moreover, the embodiment as depicted in FIG. 6 features a multiplicity of surface segments having of substantially equal size due to the 90° rotation of the first layer 12 with respect to the third layer 16. For instance, the two surface segments 5040 and 7060 are of substantially equal size. When exposed to the ambient parameter or ambient condition, the surface segments 5040 and 7060 typically exhibit an identical or at least highly similar diffusion behaviour. This way, a kind of a two-fold redundancy can be provided and/or the measurable conductivity of the two interrelated surface segments 5040, 7060 can be used to determine an average value.

As already indicated, the present sensor arrangement 10 is not only applicable to determine and to monitor a temperature history, to which the sensor arrangement 10 has been exposed to. Moreover, the sensor arrangement 10 can be used as a humidity sensor by making use of a molecular component as the dopant substance 22 which exhibits a chemical reaction when exposed to $H_2O$. Then, a residual component of a chemical reaction and/or a reaction product may diffuse into the second layer 14 after the sensor arrangement 10 has been exposed to humidity. For this purpose, at least one of first or third layers should be in contact with the ambient atmosphere.

Additionally, the sensor arrangement may be also suitable to detect the chemical constitution in the ambient environment. Hence, the sensor arrangement may also be applicable as a gas sensor, wherein at least one of the layers 12, 14, 16 is susceptible to receive and/or to embed a gaseous substance being present in the ambient atmosphere. For instance, molecular oxygen or other gases may diffuse into and through the first layer 12 towards the second layer 14 as soon as the sensor arrangement is exposed to an ambient atmosphere.

Figure 7:
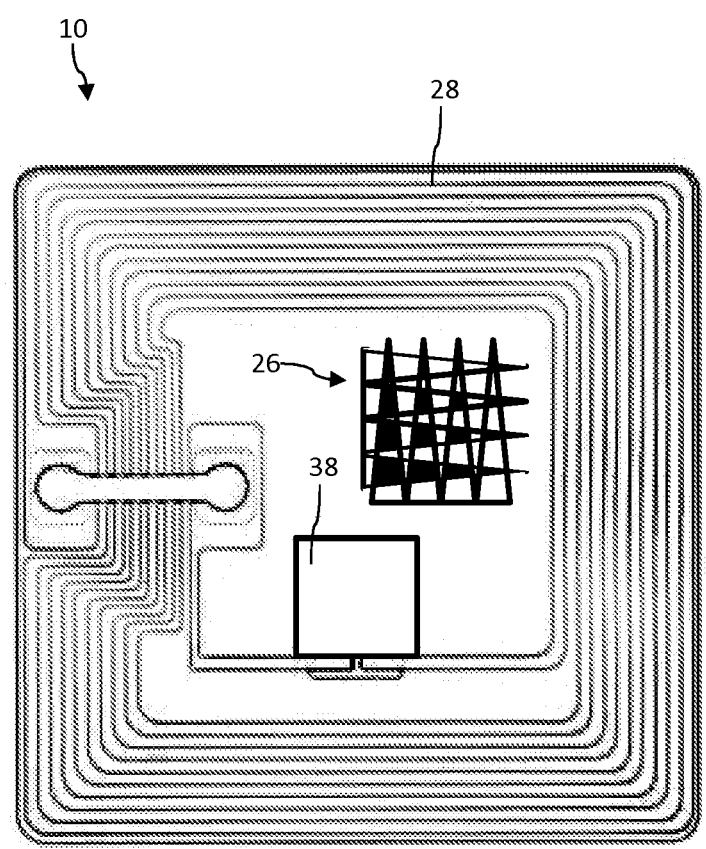

FIG. 7 finally shows the sensor arrangement 10 further comprising an antenna circuit 28 and a processing unit 38. The antenna circuit 28 is particularly adapted to receive and/or to transmit a power signal, from which electrical power can be derived to determine the conductivity of the second layer 14 of the stack 26 of layers 12, 14, 16. Hence, the entire sensor arrangement 10 may be designed as a passive RFID tag which does not require an on-site power source but which is only activated when disposed in the broadcasting area of an RFID reading arrangement.

Generally, the sensor arrangement 10 does not require an own power source since the diffusion process between the layers 12, 14, 16 is only governed and controlled by the ambient conditions that are to be monitored and measured.

The invention claimed is:

1. A sensor arrangement for monitoring an ambient parameter, the sensor arrangement comprising:
 a first layer having a diffusible component within the first layer,
 a second layer exhibiting an electrical conductivity that is dependent on a concentration of the diffusible component within the second layer, wherein at least a portion of the second layer is in direct contact with the first layer, and wherein diffusion of the diffusible component from the first layer to the second layer is dependent on the ambient parameter, and
 a third layer in contact with a surface of the second layer that faces away from the first layer, wherein the first layer and the third layer each comprise at least two geometrical non-overlapping structures lying in the plane of the respective layer, wherein the at least two geometrical non-overlapping structures are separated by a filling material or by a void space, and wherein the at least two geometrical non-overlapping structures of the first layer at least partially overlap with the at least two geometrical non-overlapping structures of the third layer and form a plurality of overlapping regions with at least one of the overlapping regions having an areal size different than an areal size of another of the overlapping regions.

2. The sensor arrangement according to claim 1, wherein the diffusion of the diffusible component is affectable by a magnitude of the ambient parameter.

3. The sensor arrangement according to claim 1, wherein the diffusible component within the first layer is adapted to diffuse towards or to diffuse into the second layer.

4. The sensor arrangement according to claim 1, wherein the first layer and the third layer are electrically connectable to a measurement device to determine the electrical conductivity of the second layer.

5. The sensor arrangement according to claim 1, wherein the ambient parameter comprises one or more of an ambient temperature, an ambient illumination, an ambient humidity or a concentration of an ambient gaseous substance.

6. The sensor arrangement according to claim 1, wherein the first layer and/or the third layer comprise a conducting or semiconducting material provided with a diffusible dopant substance.

7. The sensor arrangement according to claim 6, wherein the diffusible dopant substance comprises a molecular component exhibiting a chemical reaction when exposed to $H_2O$.

8. The sensor arrangement according to claim 1, wherein the first layer and/or the third layer comprise an organic semiconductor.

9. The sensor arrangement according to claim 1, wherein a total area of contact between the first layer and the second layer is unequal to a total area of contact between the second layer and the third layer.

10. The sensor arrangement according to claim 1, wherein the at least two geometrical non-overlapping structures of the first layer comprise a first geometric shape and the at least two geometrical non-overlapping structures of the third layer comprise a second geometric shape having a shape that is substantially identical to that of the first geometric shape, and wherein an orientation of the first geometric shape in the first layer is rotated with respect to an orientation of the second geometric shape in the third layer by a predefined angle about a rotation axis extending substantially parallel to the surface normal (z) of the first and/or the third layer.

11. The sensor arrangement according to claim 1, further comprising a processing unit configured to determine the electrical conductivity of the second layer.

12. A packaging for at least one item, comprising at least one sensor arrangement according to claim 1.

13. The sensor arrangement according to claim 1, further comprising an antenna circuit separate from the first and second layers, wherein the antenna circuit is configured to:
receive a power signal, and
use the power signal to determine the electrical conductivity of the second layer.

14. The sensor arrangement according to claim 1, wherein each of overlapping regions has an areal size different than that of every other one of the plurality of overlapping regions.

15. A sensor arrangement for monitoring an ambient parameter, the sensor arrangement comprising:
a first layer having a diffusible component within the first layer,
a second layer exhibiting an electrical conductivity that is dependent on a concentration of the diffusible component within the second layer wherein at least a portion of the second layer is in direct contact with the first layer,
a third layer, wherein at least a portion of the third layer is in direct contact with a surface of the second layer that faces away from the first layer,
wherein the first layer has numerous triangular shaped geometrical structures that are adjacently disposed in the plane of the first layer,
wherein the third layer has numerous triangular shaped geometrical structures that are adjacently disposed in the plane of the third layer, and
wherein the geometrical structures of the first layer are rotated by a predefined angle relative to the geometrical structures of the third layer thereby forming substantially overlapping surface segments of the first and the third layers.

16. The sensor arrangement according the claim 15, wherein the triangular shaped geometrical structures of the first layer are oriented parallel with respect to each other.

17. The sensor arrangement according to claim 15, wherein the triangular shaped geometrical structures of the third layer are oriented parallel with respect to each other.

18. The sensor arrangement according to claim 15, wherein the geometrical structures of the first layer and of the third layer form a pattern comprising at least two surface segments of different size.

* * * * *

UNITED STATES PATENT AND TRADEMARK OFFICE
CERTIFICATE OF CORRECTION

PATENT NO. : 10,215,786 B2
APPLICATION NO. : 14/367828
DATED : February 26, 2019
INVENTOR(S) : Hardy Kietzmann et al.

Page 1 of 1

It is certified that error appears in the above-identified patent and that said Letters Patent is hereby corrected as shown below:

On the Title Page

Item [71], Applicant:
Replace Applicant's city of residence listed as "Frankfurt" with --Frankfurt am Main--.

In the Claims

At Column 16, Claim 14, Line number 10, replace "each of overlapping regions" with --each of the plurality of overlapping regions--.

At Column 16, Claim 15, Line number 19, replace "within the second layer wherein" with --within the second layer, wherein--.

Signed and Sealed this
Twelfth Day of November, 2019

Andrei Iancu
*Director of the United States Patent and Trademark Office*